United States Patent [19]

Lindner

[11] Patent Number: 4,652,672

[45] Date of Patent: Mar. 24, 1987

[54] TARTARIC ACID MONOESTERS OF ALKANOLAMINES

[76] Inventor: Wolfgang F. Lindner, St. Veiter-Anger 22, Graz, Austria, A-8046

[21] Appl. No.: 542,729

[22] Filed: Oct. 17, 1983

[30] Foreign Application Priority Data

Aug. 19, 1983 [DE] Fed. Rep. of Germany ....... 3330005

[51] Int. Cl.$^4$ ...................... C07C 93/04; C07C 93/06; C07C 93/187; C07C 93/20
[52] U.S. Cl. .................................... 560/180; 544/134; 548/444; 558/414; 558/416; 560/20; 560/60; 560/106; 560/112; 560/182; 564/349
[58] Field of Search ..................... 564/349; 560/20, 60, 560/106, 180, 182, 11; 558/414, 416

[56] References Cited

U.S. PATENT DOCUMENTS 3,337,628  8/1967  Crowther et al. ................... 564/349
4,039,685  8/1977  Köppe et al. ........................ 564/304

OTHER PUBLICATIONS

Newman, *Optical Resolution Procedures for Chemical Compounds*, vol. 3, Manhattan College, Riverdale, N.Y. (1984), pp. 7–15.

*Synthetic Organic Chemicals* (1932), vol. V, No. 5, Eastman Kodak Company.
*The Merck Index*, 9th ed., No. 7628 (1976).
Lucas, *Organic Chemistry*, 2nd ed., pp. 313, 314.

*Primary Examiner*—Robert W. Ramsuer

[57] ABSTRACT

For the analytical and preparative separation of the optical isomers of optically active alkanolamines into their optically pure antipodes a new resolution method is presented which involves an ester formation of the alkanolamines with optically pure and symmetrically O,O disubstituted (R,R)- or (S,S)-tartaric acids. The derivitization reactions are carried out in aprotic solvents and the primary and secondary functions are blocked via ion-pair formations with strong acids, e.g. dichloroacetic acid. The tartaric acid anhydrides are predominantly used as reagents but other ester formation methods are also practicable. The mixture of the diastereomeric alkanolamine tartaric acid monoesters are separable into their optically active and pure isomers by various chromotographic separation techniques, e.g. straight or reverse phase LC, but also by extraction methods e.g. Soxhlet extraction. The optically pure parent alkanolamine isomers can be obtained by ester hydrolysis, with high yield, from the optically pure fractions of the alkanolamine tartaric acid monoesters.

5 Claims, No Drawings

TARTARIC ACID MONOESTERS OF ALKANOLAMINES

The invention relates to tartaric acid monoesters of optically active, substituted alkanolamines, to a method for their synthesis and also to their use for the synthesis of optically pure alkanolamines from the tartaric acid monoesters.

Some substituted alkanolamines are known having the general formula

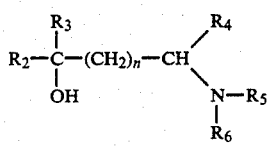

in which:
- n can have the value nought to four,
- $R_2$ signifies alkyl, aralkyl, aryl, methylene fluorenone oxime ether, the group $R_7$-oxyalkyl, wherein $R_7$ is aryl or a heterocyclic radical and wherein the radicals can in each case be substituted, or hydrogen,
- $R_3$ signifies aryl, alkyl, cycloalkyl, wherein the radicals can in each case be substituted, or hydrogen,
- $R_4$ signifies alkyl, aryl, wherein the radicals can in each case be substituted, or hydrogen,
- $R_5$ and $R_6$, which can either be the same or different, signify straight chained, branched or cyclic alkyl, a five or six membered nitrogen containing heterocycle, aralkyl or amino alkyl carbonyl, wherein the radicals can in each case be substituted, or hydrogen and in which the radicals $R_2$ to $R_6$ can be linked with one another in ring-like manner.

Substituted ethanolamines and propanolamines in particular have great pharmaceutical significance as cardiaca.

Various methods are known for the synthesis of optically pure substituted alkanolamines. One can thus obtain optically more or less pure alkanolamines either
(a) by asymmetrical synthesis or
(b) by synthesizing the racemic mixture and subsequently subjecting it to racemic separation techniques of racemates by the direct or indirect routes.

Group (a) embraces the possibility of starting from an optically active compound which, by way of example, is present as an optically pure natural product, such as D-mannitol, which is then split by an oxidation to the optically active C3 fragment, the glycidyl group. The optically active ethanolamines or propanolamines are then sythesised from the latter. (See German Offenlegungsschrift No. 28 10 732).

There also exists the possibility of obtaining optically active compounds via stereospecific reactions, such as stereospecific catalysis, induction or inversion. In contrast to the above method this route however hardly leads to optical yields of the end product of greater than 98% if one does not also make use of separation methods of optical isomers by the direct or indirect route as in method (b) (see D. Valentine and I. W. Scott, Review "Asymmetric Organic Synthesis", Synthesis (1978), page 329).

Racemic separations in accordance with method (b) have already been described with reference to examples of the alkanolamines used as β-blockers. The indirect route of racemic separation consists of synthesizing diastereoisomeric reaction products from the racemic enantiomeric product (for example with free primary or secondary amino group) with optically pure reaction partners, and then separating these reaction products into their optically isomeric forms, preferably by chromatography. Aryl alkyl isocyanates (for example S(−)-1-phenyl ethyl isocyanate) (see W. Dieterle and W. Faigle, Journal of Chromatography 259 (1983) 311), acidic halogenides of optically active acids (for example N-trifluoracetyl-L-prolyl-chloride) (see S. Caccia et al., Journal of Chromatographic Science (1978) 543) or reactive N-blocked amino acid derivatives (for example the symmetric anhydride of BOC-L-Leucin (see J. Hermansson and C. von Bahr, Journal of Chromatography 227 (1982) 113) are used as the optically active reagents. For preparative purposes all these reagents have however the disadvantage of a high price and usually lead to products with an amide structure element. The diastereoisomeric derivatives synthesized in accordance with these methods preferably serve for analytical purposes and are chromatographised by normal phase separating systems, such as silica gel or by reversed phased separating systems, for example RP 18-separating system. Gas chromatography can also be used in particular cases. The selectivity factors $\alpha$, as a value for the separation of the pairs of the diastereoisomeric derivatives are generally just sufficient to obtain a base line separation in analytical separating systems. Furthermore a hydrolysis of the amide structure elements to the optically pure alkanolamines is only possible under quite drastic reaction conditions, whereby the danger of racemisation and decomposition always exists.

Another direct separating method of racemates is the possibility of reacting racemic alkanolamines with optically active acids to form diastereoisomeric salts which have different crystallization characteristics (different lipophily) (process of the stereospecific fractionated crystallization). In this case however repeated crystallization steps, which mostly lead to significant losses, are however necessary to obtain end products with high optical purity. After separation the alkanolamines can be readily recovered from the salts by alkylization. By way of example campher-10-sulfonic acid (see P. Newman, Optical Resolution Procedures for Chemical Compounds, vol. 1, Optical Resolution Information Center, New York, 10471), (R,R)- or (S,S)-O,O-dibenzoyl tartaric acid or (R,R)- or (S,S)-O,O-ditoluoyl tartaric acid (see T. Leigh, Chem. Ind. London, 36 (1977) or R. Howe, British Pat. No. 1,069,343 (1967)) can serve as the optically active acids. Under specific conditions chromatographic separation of the enantiomeric salts and/or particular propanolamines can also be used instead of stereospecific crystallization. However the selectivity factors are low and therefore a preparative application is hardly possible.

The object underlying the present invention is to prepare diastereoisomeric tartaric acid monoesters from optically active racemic alkanolamines.

The optically isomeric forms of these diastereoisomeric tartaric acid monoesters have chemical and physical characteristics which differ surprisingly strongly from each other and which now make it possible to separate the pairs of optically isomeric forms into the optically pure compounds in simple manner. Finally one can hydrolise the separated, and now optically pure, tartaric acid esters in a simple manner while retaining the optically active center to form the corresponding optically pure alkanolamines. High optical yields are obtainable. With this method the optical purity of the alkanolamines as well as of their tartaric acid derivatives can also be simultaneously controlled in simple manner.

When the alkanolamines, racemic or optically pure, are pharmacologically active then their corresponding tartaric acid esters also show pharmacological activity which will preferably be that underlying the alkanolamines. Thus these tartaric acid esters of the alkanolamines can also be regarded as their prodrug form.

In accordance with the invention tartaric acid monoesters of optically active, substituted alkanolamines and salts thereof are proposed with the general formula

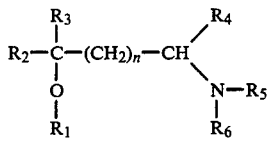

wherein:

n can have the value nought to four, $R_1$ signifies (R,R) tartryl or (S,S) tartryl, wherein an organic radical is substituted for the hydrogen of the hydroxyl groups, $R_2$ signifies alkyl, aralkyl, aryl, methylene fluorenone oxime ether, the group $R_7$-oxyalkyl, wherein $R_7$ is aryl or a heterocyclic radical, and wherein the radicals can in each case be substituted, or hydrogen, $R_3$ signifies aryl, alkyl, cycloalkyl, wherein the radicals can in each case be substituted, or hydrogen, $R_4$ signifies alkyl, aryl, wherein the radicals can in each case be substituted, or hydrogen, $R_5$ and $R_6$, which can either be the same or different, signify straight chained, branched or cyclic alkyl, a five or six member nitrogen containing heterocycle, aralkyl or amino alkyl carbonyl, wherein the radicals can in each case be substituted, or hydrogen and in which the radicals $R_2$ to $R_6$ can be linked with one another in ring-like manner.

The inventor has thus discovered that the optically active racemic tartaric acid monoesters of racemic alkanolamines are highly and easily separable into their optically active isomers under diverse conditions. The optically pure alkanolamines can furthermore easily be prepared by simple ester hydrolysis of the separated tartaric acid monoesters.

These tartaric acid monoesters can be produced in the form of the diastereoisomeric ester mixture by reacting a racemic alkanolamine of the general formula

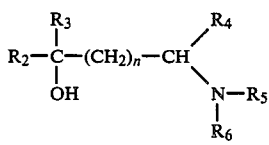

with an (R,R)-O,O substituted tartaric acid or with an (S,S)-O,O substituted tartaric acid in the presence of a condensation agent, or with an anhydride or acid halogenide of the above acids in the melt or in an aprotic solvent.

Preferably the conversion is effected with the anhydride of the acids in an aprotic solvent at temperatures from room temperature to 150° C. The temperature that is used in any particular case depends on the solvent that is used and also on the reaction partners. It preferably lies in the range from 40° to 90° C. The acids or acid derivatives are used either in equimolar quantities or in excess.

By reacting racemic alkanolamines with optically pure O,O substituted tartaric acid derivatives, for example anhydrides, the diastereoisomeric O-derivatives arise surprisingly instead of the N-derivatives when one operates in an aprotic medium with the addition of a further free acid, such as toluene sulfonic acid or trichloroacetic acid. Without the addition of acid one obtains, in addition to the O-derivatives, also N-derivatives and mixtures thereof, from the which O- and N-derivatives can however be separately isolated.

Dichloromethane, 1,2-dichloroethane, acetone, acetonitrile, toluene, dimethyl formamide, dimethyl sulfoxide, tetrahydrofuran, dioxane, ethylene glycol dimethylether or N-methyl-pyrrolidone-2 can preferably be used as aprotic solvents. The solvents are preferably used in the anhydrous state.

Dicyclohexyl carbodiimide, tosyl chloride, trifluoro acetic acid anhydride, sulfuryl chloride, $DMF/SOCl_2$, aluminium oxide and also molecular sieves can be considered as condensation agents. If alkanolamines with primary or secondary amino groups are used for the reaction, i.e. if $R_5$ and/or $R_6$ is hydrogen, the amino group is preferably protected prior to esterification in order to suppress as far as possible the competing reaction, namely the amide formation. For this purpose protective groups can be used which can later be easily removed again. Preferably the amino group is protected by salt formation. For salt formation, strong inorganic or organic acids are used which form with the amino group an ion pair which only weakly dissociates in the aprotic solvents. By way of example sulfonic acids and halogen carboxylic acids can be considered for use as organic acids and hydrohalogenic acids can be considered for use as inorganic acids. One preferably uses toluene sulfonic acid, trichloro acetic acid and trifluoro acetic acid as the organic acid and hydrochloric acid as the inorganic acid. The amino groups can be converted into the free form by weak bases after the esterification reaction or after the separation of the diastereoisomeric ester mixture. The amino groups can also be simultaneously converted into the free form during the hydrolytic cleavage of the tartaric acid monoesters for the production of the optically pure alkanolamines.

The tartaric acid monoesters of the alkanolamines that are formed can be crystallized from the aqueous medium, preferably in the pH range from 0 to 9, or can be extracted by means of organic solvents, preferably dichloromethane or dichloroethane.

The optically isomeric forms can be obtained from the resulting disatereoisomeric ester mixture by subjecting the esterification mixture to selective crystallization or extraction, or they can be separated by chromatographic routes.

For fractionated crystallization a solvent is selected which dissolves the optically isomeric forms to different extents. As solvents one considers halagenated hydrocarbons such as dichloromethane, ketones such as acetone, ether, esters such as ethylacetate, secondary and tertiary alcohols such as isopropanol, or water or aqueous buffer solutions. The most suitable solvent in each particular case depends on the tartaric acid ester concerned. After 1 to 4 crystallization steps one mainly succeeds in reaching optically pure tartaric acid esters.

The separation preferably takes place by extraction or chromatography. For the extraction an extraction agent is used which dissolves the optically isomeric forms to different extents. As extraction agents one can consider halogenated hydrocarbons such as ketones, ether, esters such as ethyl acetate, dichloromethane, secondary and tertiary alcohols, or water (aqueous buffer solution). Preferably acetone, isopropanol, dichloromethane, dichloroethane, ethyl acetate, cyclohexane, toluene, THF, dioxane or aqueous organic or inorganic buffer solutions, such as alkali buffers or ammonium phosphate buffers, are used.

For the chromatographic method (column chromatography, thin layer chromatography, high pressure liquid chromatography) the separation can be performed both in normal phase (for example silica gel) or also in the reverse phase modes, for example RP 18 (Reverse Phase, Octadecyl). Acetone, isopropanol, dichloromethane, cyclohexane and toluene, and also different mixtures of these, are used as the mobile phases for silica gel columns or plates and acidic buffers mixed with methanol or acetonitrile are used for the reverse phases. O,O symmetrically disubstituted (R,R) or (S,S) tartaric acids or their anhydrides and acidic chlorides are used for the synthesis of the tartaric acid monoesters of the invention. Acyl, alkyl, aryl, imidomethyl, aralkyl, heteroaryl, tosyl, trialkyl silyl or alkylidene can be considered as substitutes for the hydrogen of the hydroxyl groups and can in each case be substituted. In the case of alkylidenes the two oxygen atoms are connected to one another via cyclical acetals being formed by reaction of the hydroxygroups with ketones, preferably acetone, or aldehydes, preferably benzaldehyde. The alkylidene radical preferably contains 1 to 2 C-atoms in the chain. A large number of groups can be used as the acyl radical in the O,O-diacyl tartaric acids for which, acetyl, benzoyl, toluoyl, nitrobenzoyl, cyclohexyl carbonyl, and trichloroacetyl are named merely by way of example. Other acyl radicals are likewise suitable. Preferably one uses acetyl, benzoyl and toluoyl.

Alkyl radicals with 1 to 5 C-atoms are preferably used as the alkyl radicals in the O,O-dialkyl tartaric acids. Particularly preferred are methyl and ethyl which can in each case be substituted. Imido groups such as the N-phthalimido radical or the N-succinimido radical can be considered as substitutes as well as halogenes such as chlorine. The aryl radical is preferably phenyl, the aralkyl radical is preferably benzyl and the heteroaryl radical is preferably pyridyl, which can in each case be substituted. The trialkyl silyl radical preferably contains alkyl groups with 1 to 3 C-atoms, particularly preferred is the trimethyl silyl radical.

n is preferably nought or one.

$R_2$ is preferably an alkyl radical with 1 to 3 C-atoms, an aralkyl radical with 7 to 10 C-atoms, aryl, methylene fluorenone oxime ether, the group $R_7$-oxymethyl, wherein the radicals can in each case be substituted, or hydrogen. The alkyl radical is preferably substituted with chlorine or with the tosyloxy radical. The aryl radical is preferably phenyl, indenyl or naphthyl which can in each case be substituted. If $R_7$ is an aryl radical it is preferably phenyl, naphthyl, indenyl or a benzocyclo alkyl such as tetralonyl, which can in each case be substituted. If $R_7$ is a heterocyclic radical it is preferably a five or six member heterocycle or a benzoheterocycle. Preferred heterocyclic radicals are 2-thioimidazolyl, carbazolyl, benzofuryl, indolyl, dihydrocarbostyrilyl which can in each case be substituted.

$R_3$ is preferably phenyl, cyclohexyl or hydrogen.

The $R_4$ radical is preferably hydrogen or alkyl with 1 to 3 C-atoms.

The radicals $R_5$ and $R_6$ which can be the same or different are preferably hydrogen, branched or straight chained alkyl with 1 to 4 C-atoms, cyclical alkyl with 4 to 6 C-atoms, phenyl alkyl with 7 to 12 C-atoms or amino alkyl carbonyl. $R_5$ is preferably hydrogen and $R_6$ hydrogen, isopropyl, n-butyl, amino methyl carbonyl, 1-phenyl-3-methyl-propyl, methyl, ethyl and dimethoxy phenylethyl. Further preferred are $R_4$ and $R_5$ hydrogen and $R_6$ isopropyl and tertiary butyl.

$R_2$ and $R_5$ can be cyclically linked together via 2 to 5 C-atoms with or without nitrogen bridges involved. In the same way $R_4$ and $R_5$ and also $R_5$ and $R_6$ can be linked together.

Preferably preferred alkanolamines for synthesizing the tartaric acid monoesters in accordance with the invention are given in table I.

As already mentioned further above the tartaric acid monoesters of the invention make available a method with which the racemic alkanolamines can be separated into the optically isomeric forms with good yields. The separated, optically isomeric forms of the alkanolamine tartaric acid monoesters can be hydrolytically cleaved under acidic conditions, for example with 0.1 to 1n aqueous or ethanolic hydrochloric acid, or under basic conditions, for example with 0.1 to 1n aqueous or methanolic NaOH, or by transesterification, for example in methanol in the temperature range between $-10°$ and $40°$ C.

Another possibility for the synthesis of optically pure alkanolamine consists in subjecting the mixture of the diastereoisomeric alkanolamine tartaric acid monoesters to a stereospecific pH controlled hydrolysis or to a stereospecific enzymatic hydrolysis. The above indicated route via the separation of the tartaric acid monoesters with subsequent hydrolysis is however preferred.

The invention will now be described in more detail with reference to the following examples:

EXAMPLE 1

Synthesis of (R,S)-propranolol-(R,R)-O,O-diacetyl tartaric acid monoester:

25.9 g (0.1 mol) of dry (R,S)-propranolol base are dissolved with 20.0 g (0.105 mol) p-toluene sulfonic acid hydrate in 300 ml 1.2-dichloroethane at room temperature and the water by distilling it off azeotropically.

32.4 g (0.15 mol) (R,R)-(+)-O,O-diacetyl tartaric acid anhydride are added to the solution at room temperature and the mixture is then stirred while refluxing it at ca. 80° C. for 24 hours.

After removing the solvent the solid residue is added to a 5% aqueous NaHCO$_3$ solution until it dissolves (ca. 200 ml) and is subsequently acidified with 1n HCl until a pH value of 2.5 is reached. The mixture of the optically isomeric forms of the diastereoisomeric tartaric acid ester (R,S)-propranolol-(R,R)-O,O-diacetyl tartaric acid monoester is precipitated or extracted with CH$_2$Cl$_2$ (3×100 ml). After removing the extraction agent one obtains a residue (yield 38 g, 80%) which is brought to crystallization using acetone.

The above procedure can also be carried out under completely identical conditions using (S,S)-(−)-O,O- diacetyl tartaric acid anhydride as the reagent and one then likewise obtains 80% yield of the corresponding mixture of the optically isomeric forms. For the separation of the mixture see examples 3 to 8.

EXAMPLE 2

Synthesis of (R,S)-propranolol-(R,R)-O,O-diacetyl tartaric acid monoester:

1.81 g (7 mM) of dry (R,S)-propranolol base are dissolved in 20 ml of dichloromethane and reacted at room temperature with 3.02 g (14 mM) (R,R)-(+)-O,O-diacetyl tartaric acid anhydride and stirred for 48 hours at room temperature.

After removal of the solvent the residue is added to 16 mM NaHCO$_3$, dissolved in 50 ml water, and is stirred at room temperature which results in a crystalline precipitate. This precipitate is isolated, washed with H$_2$O and is pure (S)-propranolol-(R,R)-O,O-diacetyl tartaric acid monoester (see fraction II example 3), which by hydrolysis gives optically pure (>98%) (S)-(−)-propranolol. The filtrate contains a mixture of diastereoisomeric (R)-propranolol-(R,R)-O,O-diacetyl tartaric acid monoester and (S)-propranolol-(R,R)-O,O-diacetyl tartaric acid monoester and can be separated into the optically isomeric forms in accordance with one of the examples 3 to 8.

Yield of fraction II: 0.7 g, 42%.

EXAMPLE 3

Separation into the optically isomeric forms of the mixture obtained in accordance with example 1 of the diastereoisomeric (R)- and (S)-propranolol-(R,R)-O,O-diacetyl tartaric acid monoesters by means of extraction:

15 g of the crystal mass consisting of the mixture of the optically isomeric forms are placed in a Soxhlet apparatus, and are repeatedly extracted with acetone while being stirred. After approximately 10 cycles with a solvent volume of approximately 300 ml, pure (S)-propranolol-(R,R)-O,O-diacetyl tartaric acid monoester (fraction II) crystallizes out in the flask whereas pure (R)-propranolol-(R,R)-O,O-diacetyl tartaric acid monoester (fraction I) remains in the Soxhlet.

Fraction I:
(R)-propranolol-(R,R)-O,O-diacetyl tartaric acid monoester
Yield 7 g; melting point 196°–198° C.

$[\alpha]_{546}^{22} = +13.5°$ (c=0.405 in DMSO)

optical purity >98%.
Fraction II:
(S)-propranolol-(R,R)-O,O-diacetyl tartaric acid monoester
yield 5 g; melting point 176°–177° C.

$[\alpha]_{546}^{22} = +33.3°$ (c=0.98 in DMSO)

optical purity >98%.
3 g of a mixture of fraction I and fraction II remain in the acetone mother liquor.
Spectroscopic data:
$^{13}$C NMR, XL 200.DMSO d$_6$, TMS as internal standard, δ (ppm).

| | Fraction I | Fraction II | (R,S)—Propanolol.HCl (in D$_2$O) |
|---|---|---|---|
| *=CH—CH=* | 73,39; 72,68 | 74,92; 73,11 | — |
| =CH—O— | 69,11 | 69,11 | 62,37 |
| —CH$_2$—O— | 67,0 | 67,13 | 66,45 |
| =CH—NH— | 48,84 | 49,72 | 47,92 |
| —CH$_2$—NH— | 43,18 | 44,46 | 43,46 |

Schematic formula A: (R)- and (S)-propranolol-(R,R)-O,O-diacetyl tartaric acid monoesters (fraction I and fraction II respectively)

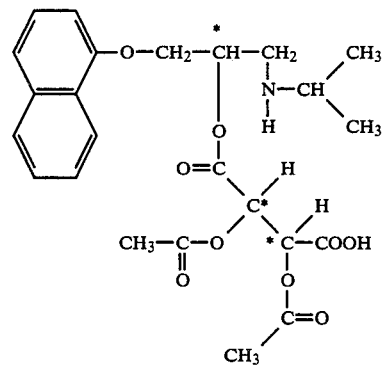

MG 475,48

The tartaric acid monoesters obtained by reacting (R,S)-propranolol with (S,S)-O,O-diacetyl tartaric acid anhydride in place of (R,R)-O,O-diacetyl tartaric acid anhydride behave, with regard to the lipophily or extractability, inversely to the above scheme of preparation, i.e. the Soxhlet residue is then (S)-propranolol-(S,S)-O,O-diacetyl tartaric acid monoester, whereas the more easily extractable fraction is the (R)-propranolol-(S,S)-O,O-diacetyl tartaric acid monoester. Such inversion characteristics of diastereoisomeric compounds have general applicability and thus also apply for all other (R,R)- and (S,S)-O,O-diacetyl tartaric acid derivatives of alkanolamines. This is also significant for analytical purposes because with the aid of this rule it is generally relatively simple to identify related pairs of optically isomeric forms as a result of the inversion of their peak ratios.

As a result of their chemical structure the alkanolamine tartaric acid monoesters can be present in their zwitter ionic form (formation of internal salts).

With strong acids, for example hydrochloric acid, the hydrochlorides can be synthesized in non-aqueous aprotic solvents.

In the same way alkaline salts or earth alkaline salts of the carboxyl function can be produced by the equivalent addition of alkali hydroxides or earth alkali hydroxides.

EXAMPLE 4

Separation into the optically isomeric forms of the mixture obtained in accordance with example 1 of the diastereoisomeric (R)- and (S)-propranolol-(R,R)-O,O-diacetyl tartaric acid monoesters using thin layer chromatography.

TLC plate: silica gel; mobile phase: acetone isopropanol 1:1 development distance: 8 cm $R_f$ value: $\dfrac{\text{fraction I } 0.23}{\text{fraction II } 0.41}$  $\alpha = 1.78$ The thin layer chromatography on silica gel can without restriction be regarded as a pilot technique for preparative and analytical column chromatography with silica gel as adsorbent, selectivity factors $\alpha$ are obtained which are at least similar.

EXAMPLE 5

Separation of the mixtures of the diastereoisomeric (R,R)-O,O-diacetyl tartaric acid monoesters of the (R,S)-alkanolamines given in table II (schematic formula see table I) with reverse phase chromatography (Reverse Phase HPLC):

The reaction of (R,S)-alkanolamine with (R,R)-O,O-diacetyl tartaric acid anhydride is carried out in accordance with examples 1 or 2, however for analytical purposes in smaller quantities. Optionally the anhydrous solvents dichloromethane, dichloroethane, tetrahydrofuran, acetone, acetonitrile or dioxane are used and removed after the reaction. The residue being redissolved in methanol as sample solvent can be analyzed directly. If protection of the amine functional group is necessary then toluene sulfonic acid, trichloro acetic acid or trifluoro acetic acid can be selected.

The reaction temperature lies, in dependence on the boiling points of the solvents, between room temperature and 80° C. and the reaction times are between 2 and 36 hours. The methanolic solutions of the mixtures of the diastereoisomeric tartaric acid monoesters that are obtained in each particular case are placed directly onto the chromatography column.

Chromatographic separation system:
  column 250×4.6 mm internal diameter packed with spherisorb RP 18,5 μum.
  Mobile phase: 2% acetic acid in $H_2O$ adjusted to pH of 3.7 with $NH_3$-methanol/50—50; flow rate 1.5 ml/min.

TABLE II

| Esters of (R) and (S) | $k'_R$ | $k'_S$ | $\alpha = \dfrac{k'_S}{k'_R}$ |
|---|---|---|---|
| Propranolol | 2,5 | 6 | 2,4 |
| Oxprenolol | 0,7 | 1,6 | 2,6 |
| Metoprolol | 0,67 | 1,67 | 2,5 |
| Celiprolol | 0,65 | 1,5 | 2,3 |
| Alprenolol | 0,7 | 1,6 | 2,3 |
| Carazolol | 0,7 | 1,5 | 2,14 |

EXAMPLE 6

Separation of the mixtures of the diastereoisomeric (R,R)-O,O-dibenzoyl tartaric acid monoesters of the (R,S)-alkanolamines given in table III using reverse phase HPLC:

The reaction of the (R,S)-alkanolamines with (R,R)-O,O-dibenzoyl tartaric acid anhydride is carried out in accordance with example 5. Chromatographic separation system:
  Column as in example 5; mobile phase: 2% acetic acid in $H_2O$ adjusted to a pH of 3.7 with $NH_3$-methanol/35–65.

TABLE III

| Esters of (R) and (S) | $k'_R$ | $k'_S$ | $\alpha = \dfrac{k'_S}{k'_R}$ |
|---|---|---|---|
| Oxprenolol | 2,38 | 6,81 | 2,87 |
| Propranolol | 4 | 11 | 2,75 |
| Metoprolol | 1,38 | 4,63 | 3,35 |
| Celiprolol | 1,13 | 3 | 2,65 |
| Acebutolol | 0,88 | 2,75 | 3,13 |
| Bunitrolol | 0,88 | 3,13 | 3,55 |
| Methypranolol | 2,13 | 8,38 | 3,93 |
| Alprenolol | 2,38 | 6,38 | 2,68 |
| Pindolol | 1,88 | 4,88 | 2,59 |
| Carazolol | 2,38 | 6,38 | 2,68 |
| Midodrin | 0,63 | 4,38 | 6,9 |
| Nifenalol | 0,63 | 3,0 | 4,8 |
| Norpropranolol | 1,63 | 4,0 | 2,5 |
| Bupranolol | 3,25 | 10,88 | 3,35 |
| Atenolol | 0,35 | 1,1 | 3,11 |
| Labetalol | 1,28 | 6,39 | 4,99 |
| Timolol | 2,33 | 6,22 | 2,67 |

EXAMPLE 7

Separation of the mixture of the diastereoisomeric (R,R)-O,O-ditoluoyl tartaric acid monoester of (R,S)-propranolol by means of reversed phase HPLC.

The reaction of the (R,S)-propranolol was carried out in accordance with example 5 using (R,R)-O,O-ditoluoyl tartaric acid anhydride. Chromatographic separation system:
  Column as in example 5; mobile phase; as in example 6

| Esters of (R) and (S) | $k'_R$ | $k'_S$ | $\alpha = \dfrac{k'_S}{k'_R}$ |
|---|---|---|---|
| Propranolol | 7,1 | 21,1 | 2,98 |

EXAMPLE 8

Separation of the mixtures of the diastereoisomeric (R,R)-O,O-dimethyl tartaric acid monoesters of the (R,S)-alkanolamines given in table IV by means of reverse phase HPLC:

The reaction of the (R,S)-alkanolamines with (R,R)-O,O-dimethyl tartaric acid anhydride is carried out in accordance with example 5. Chromatographic separation system: Column as in example 5; mobile phase: 2% ammonium acetate (pH 3,7)-MeOH/65–35.

TABLE IV

| Esters of (R) and (S) | $k'_R$ | $k'_S$ | $\alpha = \dfrac{k'_S}{k'_R}$ |
|---|---|---|---|
| Mobile Phase 65–35 | | | |
| Propranolol | 5,8 | 8,7 | 1,5 |
| Oxprenolol | 1,5 | 2,17 | 1,4 |
| Pindolol | 0,94 | 1,33 | 1,41 |
| Metoprolol | 2,8 | 4,0 | 1,42 |
| Celiprolol | 3,16 | 4,33 | 1,37 |
| Norpropranol | 6,11 | 10,22 | 1,67 |
| Labetalol | 6,05 | 8,33 | 1,37 |
| Bunitrolol | 1,61 | 2,16 | 1,34 |
| Alprenolol | 5,05 | 7,0 | 1,38 |
| Nifenalol | 0,38 | 0,72 | 1,89 |
| Acebutolol | 1,61 | 2,61 | 1,62 |
| Carazolol | 4,22 | 6,77 | 1,6 |
| Timolol | 2,33 | 3,16 | 1,35 |
| Oxprenolol | 5,11 | 7,0 | 1,37 |
| Methypranolol | 9,0 | 14,1 | 1,57 |
| Mobile Phase 50—50 | | | |

TABLE IV-continued

| | | | |
|---|---|---|---|
| Propranolol | 2,18 | 3,37 | 1,54 |
| Pindolol | 0,66 | 1,11 | 1,68 |

| | $k'_1$ | $k'_2$ | $\alpha = \dfrac{k'_2}{k'_1}$ |
|---|---|---|---|
| Mobile Phase 80–20 | | | |
| 1-Amino-propanol-2 | 0,66 | 1,55 | 2,35 |

| | $k'_R$ | $k'_S$ | $\alpha = \dfrac{k'_S}{k'_R}$ |
|---|---|---|---|
| Mobile Phase 90–10 | | | |
| Atenolol | 6,55 | 9,33 | 1,42 |
| Sotalol | 2,66 | 4,11 | 1,54 |

EXAMPLE 9

Hydrolytic cleavage of (R)-propranolol-(R,R)-O,O-diacetyl tartaric acid monoester:

5 g (R)-propranolol-(R,R)-O,O-diacetyl tartaric acid monoester (see fraction I of example 3) are dissolved at room temperature in 50 ml methanolic NaOH (1,5 g NaOH pellets dissolved in 50 ml methanol). After a reaction time of 1 hour the precipitate which has formed is separated off and the mother liquid is reduced to dryness. The residue is dissolved with 1n aqueous HCl and brought to pH of 9,0 with ammonia Pure (R)-(+)-propranolol precipitates.

Yield 2,5 g (88%);
melting point 73° C.

$[\alpha]_D^{20} + 8,33°$ (c=1,0 in EtOH 95%)

Optical purity >98%.

EXAMPLE 10

Hydrolytic cleavage of (S)-propranolol-(R,R)-O,O-diacetyl tartaric acid monoester:

2.5 g (S)-propranolol-(R,R)-O,O-diacetyl tartaric acid monoester (see fraction II of example 3) are dissolved in 30 ml ca. 1n methanolic hydrochloric acid at room temperature and allowed to stand for 24 hours. The solution is concentrated to dryness, the residue is put into water and ammonia is added which results in the precipitation of pure (S)-(−)-propranolol.

Yield 1.2 g (85%); melting point, 72° to 73° C.;

$[\alpha]_D^{20} - 8,32°$ (c=1,0 in EtOH 95%)

Optical purity >98%.

EXAMPLE 11

Synthesis of (R,S)-propranolol-(R,R)-O,O-diacetyl tartaric acid monoester:

2.34 (10 mMol) (R,R)-O,O-diacetyl tartaric acids are suspended in 15 ml dichloromethane and 1.72 g (10 mMol) anhydrous toluene sulfonic acid is added. A solution of 1,3 g (R,S)-propranolol (5 mMol) in 10 ml dichloromethane is then dropped into the resulting mixture while stirring, and subsequently a solution of 2.06 g dicyclohexyl carbodiimide in 15 ml of dichloromethane. The mixture is stirred at room temperature for 24 hours, filtrated by suction and the filtrate is washed with 15 ml and 10 ml of water. The organic phase is dried and the solvent is evaporated. The residue is treated with an aqueous NaHCO3 solution. The filtered aqueous solution is acidified to pH 3 and the mixture of the diastereoisomeric pairs of the tartaric acid ester is extracted with dichloromethane. The solution is then concentrated and the residue is suspended in acetone. The further working up of the reaction product in order to separate the diastereoisomeric optically isomeric pairs into the fractions I and II can take place in accordance with the examples 3 to 8

EXAMPLE 12

Synthesis of (R,S)-metoprolol-(R,R)-O,O-dibenzoyl tartaric acid monoester:

7 g (26 mMol) (R,S)-metoprolol base are dissolved together with 4.4 g (27 mMol) trichloro acetic acid in 150 ml 1,2-dichloroethane at room temperature. One adds 18 g (53 mMol) (R,R)-O,O-dibenzoyl tartaric acid anhydride to the solution and heats the solution to ca. 80° C. for 2 hours. After cooling one filters the solution from the excess reagent and concentrates the remaining solution to dryness. The residue is put into 50 ml acetone and 100 ml aqueous 10% NaHCO3 solution which results in a precipitate which contains a mixture of the tartaric acid monoesters of (R)- and (S)-metoprolol.

After filtering and washing the precipitate with H2O the latter is suspended in 100 ml acetone an is stirred for approximately 1 hour at room temperature. The precipitate is again filtered off and represents the above named mixture of esters, with the proportion of (R)-metolprolol-(R,R)-O,O-dibenzoyl tartaric acid monoester (fraction A) predominating. The corresponding (S)-metoprololester (fraction B) is present in enriched form in the acetone phase which is concentrated to dryness.

The purification of the individual metoprolol fractions (A) and (B) takes place in accordance with example 13.

Total yield of fraction (A) together with fraction (B): 12.8 g (80%).

Schematic formula: (R)- and (S)-metoprolol-(R,R)-O,O-dibenzoyl tartaric acid monoester (fraction (A) and fraction (B) respectively)

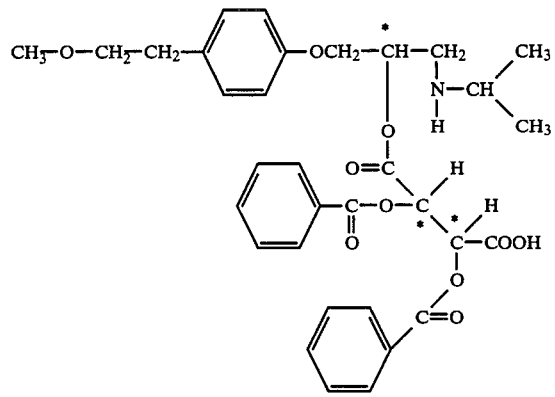

MG: 607

EXAMPLE 13

Separation of the diastereoisomeric mixture of (R)- and (S)-metroprolol-(R,R)-O,O-dibenzoyl tartaric acid monoesters into the optically isomeric forms using adsorption chromatography on silica gels:

5 g of the mixture of fraction (A) and fraction (B) (see example 12) are dissolved in 20 ml of acetone and put onto a prepared silica gel column (content ca. 350 g silica gel 70–230 mesh), which is present in acetone, and is eluated with acetone. Fraction (B) eluates before fraction (A) and in this way it is possible to isolate fraction (B) in good yield and in pure form.

Fraction (B): (S)-metoprolol-(R,R)-O,O-dibenzoyl tartaric acid monoester.

Yield: 2.1 g $[\alpha]_{546}^{31} = -57,2°$ (c=1,0 CHCl$_3$)

optical purity >98%

$^1$H-NMR (DMSO-d$_6$), δ, ppm, TMS as internal standard.

| | ester | |
|---|---|---|
| | asymmetric-CH of the tartaric acid | |
| Fraction A | 6.30 (d,1H,3Hz); 5.91(d,1H,3Hz) | 3.90(m,2H,CH$_2$O) |
| Fraction B | 5.45 (d,1H,8Hz); 5.33(d,1H,8Hz) | 4.16(m,2H,CH$_2$O) |

EXAMPLE 14

Separation of the diastereoisomeric mixture of (R)- and (S)-metoprolol-(R,R)-O,O-dibenzoyl tartaric acid monoesters into the optically isomeric forms by means of thin layer chromatography:

TLC plate: silica gel

| | R$_f$ value | | |
|---|---|---|---|
| Mobile phase: | Fraction A | Fraction B | |
| Acetone | 0,09 | 0,21 | 2,3 |
| Acetone-dioxane/ 9:1 | 0,16 | 0,34 | 2,1 |
| Acetone-dioxane/ 1:1 | 0,54 | 1 | 1,9 |

EXAMPLE 15

Hydrolytic cleavage of (S)-metoprolol-(R,R)-O,O-dibenzoyl tartaric acid monoester:

2.3 g (S)-metoprolol-(R,R)-O,O-dibenzoyl tartaric acid monoester (see example 13, fraction (B) are added at room temperature to 70 ml methanolic KOH (0,84 g KOH pellets dissolved in 70 ml methanol) and stirred for 30 minutes. Thereafter the solution is brought with hydrochloric acid to a pH value of 7.0 and the methanol is removed by evaporation. 70 ml of water diluted ammonia is added to the residue and the solution is extracted with ether. From the dried ether solution one obtains pure (S)-(−)-metoprolol (base).

$[\alpha]_{546}^{31} = -9,0°$ (c=1,0 CHCl$_3$)

EXAMPLE 16

Separation of the mixtures of the diastereoisomeric (R,R)-O,O-dibenzyl tartaric acid monoesters of the (R,S) alkanolamines given in table V by using reverse phase HPLC:

The reaction of the alkanolamines with (R,R)-O,O-dibenzyl tartaric acid anhydride is carried out in accordance with example 5.

Chromatographic separation system:
Mobile phase: 2% acetic acid in H$_2$O adjusted to a pH of 3.7 with NH$_3$-methanol/65–35.
Column as in example 5.

TABLE V

| Esters of (R) and (S) | k'$_1$ | k'$_2$ | $\alpha = \dfrac{k'_2}{k'_1}$ |
|---|---|---|---|
| Mobile Phase 65–35 | | | |
| 2-amino-1-propanol | 10,8 | 21,0 | 2,13 |
| 1-amino-2-propanol | 2,88 | 4,77 | 1,66 |
| 3-hydroxy-pyrrolidin | 4,55 | 6,77 | 1,49 |
| 3-hydroxy-N—methyl-piperidine | 4,77 | 7,33 | 1,53 |
| | k'$_R$ | k'$_S$ | $\alpha = \dfrac{k'_S}{k'_R}$ |
| Mobile Phase 50—50 | | | |
| Acebutolol | 9,55 | 20,11 | 2,1 |

TABLE I

| | R$_3$, R$_4$, R$_5$ = H; n = 0 | Name of the |
|---|---|---|
| R$_2$ | R$_6$ | alkanolamines |
|  | Isopropyl | Propranolol |
|  | Isopropyl | Pindolol |
| 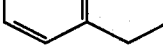 | Isopropyl | Oxprenolol |

TABLE I-continued

| R₃, R₄, R₅ = H; n = 0 | | Name of the |
|---|---|---|
| R₂ | R₆ | alkanolamines |
| —CH₂—O—C₆H₄(o-CH₂—CH=CH₂) | Isopropyl | Alprenolol |
| —CH₂—O—C₆H₄(p-CH₂—CH₂—O—CH₃) | Isopropyl | Metoprolol |
| —CH₂—O—C₆H₃(o-CO—CH₃)(p-NH—CO—CH₂—CH₂—CH₃) | Isopropyl | Acebutolol |
| —CH₂—O—C₆H₄(p-CH₂—C(=O)—NH₂) | Isopropyl | Atenolol |
| —CH₂—O—C(=N—S—N=)(morpholino) (1,2,5-thiadiazole with morpholine) | t-Butyl | Timolol |
| —CH₂—O—C₆H₄(m-CH₃) | Isopropyl | Toliprolol |
| —CH₂—O—C₆H₄(p-NH—C(=O)—CH₃) | Isopropyl | Practolol |
| —CH₂—O—(carbazol-4-yl) | Isopropyl | Carazolol |
| —C₆H₄(p-NH—SO₂—CH₃) | Isopropyl | Sotalol |

TABLE I-continued
| R₃, R₄, R₅ = H; n = 0 | | Name of the |
|---|---|---|
| R₂ | R₆ | alkanolamines |
| 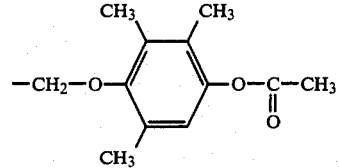 | Isopropyl | Methylpranolol |
| 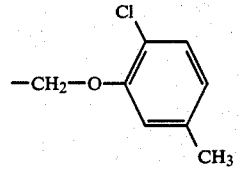 | t-Butyl | Bupranolol |
| 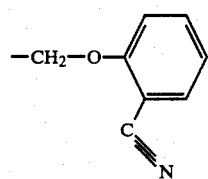 | t-Butyl | Bunitrolol |
| 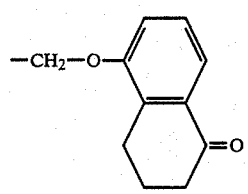 | t-Butyl | Bunolol |
| 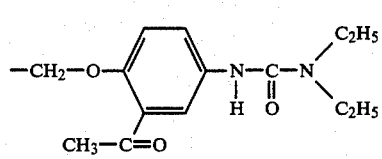 | t-butyl | Celiprolol |
| 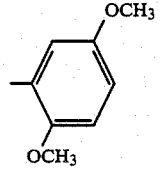 | —CO—CH₂NH₂ | Midodrin |
| 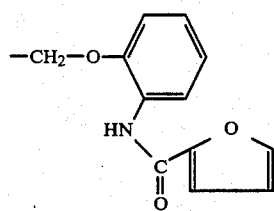 | t-Butyl | Ancarolol |
| 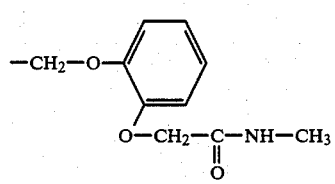 | t-Butyl | Cetamolol |

TABLE I-continued

| R₂ | R₆ | Name of the alkanolamines |
|---|---|---|
| fluorenyl =N—O—CH₂— | t-Butyl | |
| 4-CH₃COO-2-OCH₂-phenyl-O-CH₂— | t-Butyl | Vanilol |
| 2-OCH₃-phenyl-O-CH₂— | Isopropyl | Moprolol |
| 2-(O-CH₂—)-benzofuran (with Ac) | Isopropyl | Befunolol |
| 4-O₂N-phenyl— | Isopropyl | Nifenalol |
| 2-naphthyl— | Isopropyl | Pronethalol |
| 2-HO-5-CONH₂-phenyl— | —CH(CH₃)—CH₂—CH₂—C₆H₅ | Labetalol |
| indanyl— | Isopropyl | Indenol |

$R_3, R_4, R_5 = H; n = 0$

TABLE I-continued
| | R₃, R₄, R₅ = H; n = 0 | Name of the |
|---|---|---|
| R₂ | R₆ | alkanolamines |
| 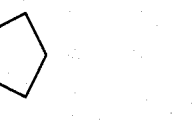 | t-Butyl | Penbutolol |
|  |  | |
| 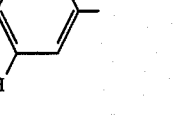 | —CH₂—CH₂—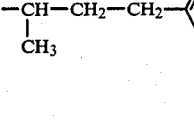 | Bometolol |
| 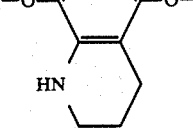 | n-Butyl or Methyl | Bamethan |
| 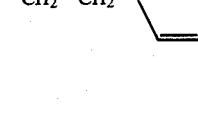 | Ethyl | |
| Cl—CH₂— | Isopropyl | |
| Tos-O—CH₂— | Isopropyl | |
| —CH₂—O—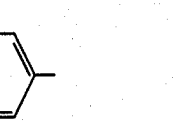 | Hydrogen | "Norpropranolol" |
| 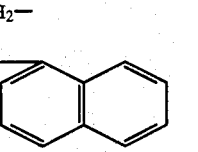 | t-Butyl | Bufuralol |
| 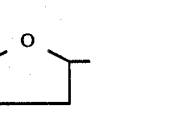 | n-Propyl | Propafenon |
| | Procyclidin | |
| 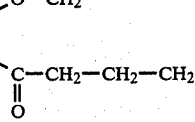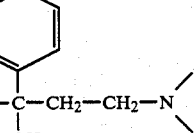 | | |

TABLE I-continued

| R₂ | R₃, R₄, R₅ = H; n = 0<br>R₆ | Name of the alkanolamines |
|---|---|---|

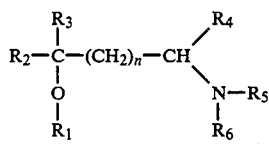

I claim:

1. Tartaric acid monoesters of optically active, substituted alkanolamines and salts thereof of the general formula $$R_2-\underset{\underset{R_1}{O}}{\overset{\overset{R_3}{|}}{C}}-(CH_2)_n-CH\overset{R_4}{\underset{\underset{R_6}{N-R_5}}{}}$$

wherein:
n is zero,
R₁ signifies
(R,R)- or (S,S)-O,O-diacyl tartryl,
(R,R)- or (S,S)-O,O-dialkyl tartryl,
(R,R)- or (S,S)-O,O-diaryl tartryl,
(R,R)- or (S,S)-O,O-diaralkyl tartryl,
(R,R)- or (S,S)-O,O-ditosyl tartryl,
and wherein the radicals can be substituted, R₂ signifies the group R₇-oxymethyl, wherein R₇ is aryl or substituted aryl,
R₃ signifies hydrogen,
R₄ signifies hydrogen,
R₅ and R₆, which can either be the same or different, signify straight or branched alkyl or hydrogen.

2. Tartaric acid monoesters in accordance with claim 1, wherein the acyl radical is acetyl, toluoyl, benzoyl or trichloroacetyl, wherein the alkyl radical contains 1 to 5 C-atoms, wherein the aryl radical is phenyl and wherein the aralkyl radical is benzyl.

3. Tartaric acid monoesters in accordance with claim 2, wherein the alkyl radical signifies methyl or ethyl.

4. Tartaric acid monoesters in accordance with claim 1 wherein
R₅ and R₆ signify hydrogen, branched or straight chained alkyl with 1 to 4 carbon atoms.

5. Tartaric acid monoesters in accordance with claim 1, wherein R₅ is hydrogen, R₆ is isopropyl or tertiary butyl.

* * * * *